(12) United States Patent
Nair

(10) Patent No.: US 11,317,831 B2
(45) Date of Patent: May 3, 2022

(54) PATIENT MONITORING SYSTEM USING WEARABLE SENSORS WITH AUTOMATED TEMPLATE MATCHING

(71) Applicant: Vishnu Nair, Lexington, MA (US)

(72) Inventor: Vishnu Nair, Lexington, MA (US)

( * ) Notice: Subject to any disclaimer, the term of this patent is extended or adjusted under 35 U.S.C. 154(b) by 277 days.

(21) Appl. No.: 16/363,142

(22) Filed: Mar. 25, 2019

(65) Prior Publication Data

US 2019/0216367 A1 Jul. 18, 2019

Related U.S. Application Data

(63) Continuation of application No. 15/361,455, filed on Nov. 27, 2016, now abandoned.

(60) Provisional application No. 62/259,403, filed on Nov. 24, 2015.

(51) Int. Cl.
*A61B 5/11* (2006.01)
*A61B 5/00* (2006.01)

(52) U.S. Cl.
CPC ........... *A61B 5/1115* (2013.01); *A61B 5/1116* (2013.01); *A61B 5/7246* (2013.01); *A61B 2562/0219* (2013.01)

(58) Field of Classification Search
CPC ... A61B 5/1115; A61B 5/1116; A61B 5/7246; A61B 2562/0219; A61B 5/1123; A61B 2505/09; A61B 2503/10; A61B 5/1118; A61B 5/024; A61B 5/1117; G06K 9/00335; G06Q 10/0639; G16H 20/30
See application file for complete search history.

(56) References Cited

U.S. PATENT DOCUMENTS

2014/0358193 A1* 12/2014 Lyons ................ A61N 1/37229
607/48
2015/0100141 A1* 4/2015 Hughes ................ A61B 5/1118
700/92

* cited by examiner

*Primary Examiner* — Patrick Fernandes
(74) *Attorney, Agent, or Firm* — BainwoodHuang

(57) ABSTRACT

A wearable patient monitoring device in a patient monitoring system includes motion sensors generating sensor output signals in response to sensed patient motion, and a processor that processes the sensor output signals according to a template-matching monitoring process that includes (1) detecting occurrence of a first event of a multi-event movement based on first values of the sensor output signals, the multi-event movement having a finite-state-machine (FSM) representation as a sequence of states corresponding to events and expected values of the sensor output signals of the multi-event movement, (2) detecting occurrence of remaining events of the multi-event movement based on a sequence of subsequent values of the sensor output signals, and (3) upon detecting a last event of the multi-event movement, generating an output signal indicating detection of the patient performing the multi-event movement. Communications circuitry communicates the detection to a higher-level computerized device of the patient monitoring system.

6 Claims, 4 Drawing Sheets

PATIENT MONITORING SYSTEM USING WEARABLE SENSORS WITH AUTOMATED TEMPLATE MATCHING

BACKGROUND

The invention is related to the field of wearable sensors for patient monitoring.

SUMMARY

Existing patient monitoring systems come in the form of bed pressure sensors, which warn medical staff when a patient's bed is unoccupied. However, there are problems with this approach. For example, if a guest comes to visit the patient and the patient sits up from the bed, then an alarm could go off. These unnecessary warnings contribute to alarm fatigue, the phenomenon of healthcare professionals ignoring constantly triggering alarms. Another problem with these older systems is that they are not wearable and hence will not work when the patient is not in the bed. They do not work, for example, when the patient is in the bathroom. Thus, there is a need for more specific activity detection that will only alert when the specific movement is identified, and that allows a patient to move normally (i.e., to use the bathroom) while maintaining desired monitoring.

Sensing technologies are currently used for many applications in modern medicine. A study from UCLA created a Perfusion-Oxygenation Monitor (1). Analyzing perfusion and blood oxygenation is essential for treating patients with circulatory problems; treatments can also become costly if the patient is not diagnosed early. This study showed that continuously monitoring patients with wearable sensors is possible, and that it can relay important information about the status of hospital patients to the medical staff.

On the detection side, a recent study reported on the usefulness of an epoch-based classifier for detecting a sit-stand transfer. The epoch-based classifier associates certain patterns in the sensory data to certain motor movements. This study showed how the data of a subject moving from a sitting position to a standing position could be matched with a certain pattern, or template. The implementation of such a classifier can be immensely helpful in deducing the state of a patient's body posture.

Wearable sensors designed for gait analysis have applications in rehabilitation and athletic training. These include gyroscopes, accelerometers, goniometers, magnetoresistive sensors and electromyography sensors, and are placed at different locations on the body. Another study on wearable sensor-based rehabilitation used three tri-axial accelerometers placed at different locations to relay angle information and identify the type of rehabilitation exercise. This study developed an exercise assessment mechanism by allowing the sensors to guide patients through their own rehabilitation exercise. Wearable technologies are also used in connection with elite sports, including an Inertial Movement Analysis (IMA) algorithm using gyroscopes and accelerometers to measure force, direction and tilt. This algorithm helps to track the movements of athletes who perform complex sequences of movements including jumping, changing direction, and accelerating. Such movements are more difficult to track using GPS or camera systems.

Presently disclosed is a template-matching technique effective in the detection of a specific target activity, such as getting out of bed (GOB), with greater sensitivity and specificity than existing methods. In one example a gyroscope sensor is used in combination with a template-based detector for patient monitoring. A data-driven approach can be successful in detecting the target activity.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

DETAILED DESCRIPTION

The entire disclosure of U.S. provisional application 62/259,403 filed Nov. 24, 2015 and entitled "Patient Monitoring System Using Wearable Sensors with Automated Template Matching" is incorporated by reference herein.

Figure 1:
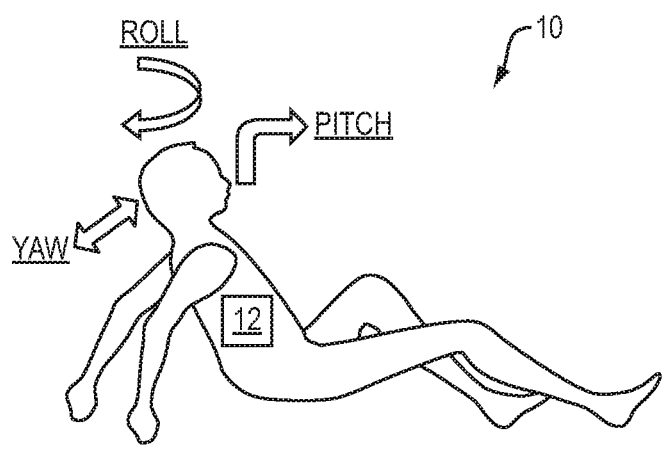
FIG. 1 is a diagram depicting axes of motion of a patient.

FIG. 1 shows a patient 10 with a wearable patient monitoring device 12, which may be secured to the patient 10 by a belt or other means. FIG. 1 shows three separate axes of movement of the patient 10, namely pitch (uprightness), roll (azimuthal orientation), and yaw (left/right lean). As described more below, the patient monitoring device 12 senses and analyzes patient motion to detect certain complex movements. In one important example, motion is analyzed for a so-called "get out of bed" or GOB movement, which can be useful in a clinical setting for alerting staff when a patient has gotten out of bed. If the patient is a fall risk or for other reasons should not be out of bed unattended, the detection of a GOB movement by the device 12 can be used to alert clinical staff who can respond appropriately. More generally, the patient monitoring device 12 uses a template approach to detecting predefined complex movements for any of a variety of reasons.

Figure 2:
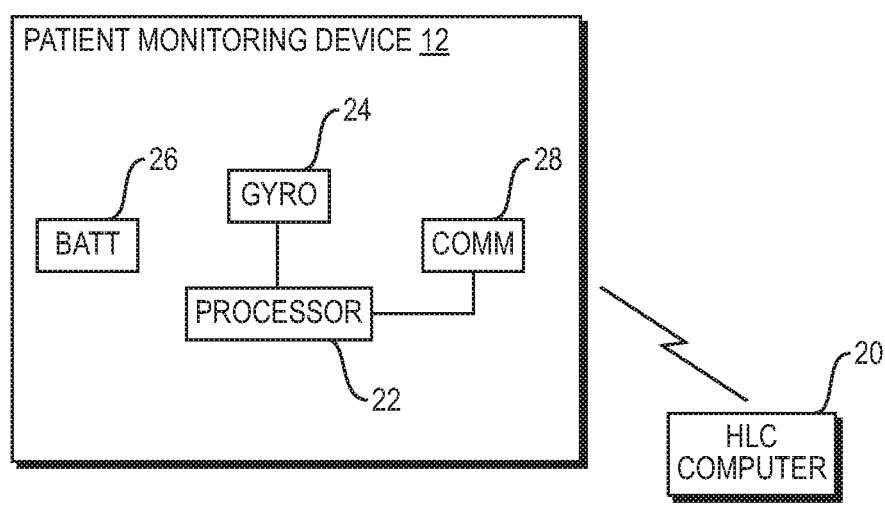
FIG. 2 is a hardware block diagram of a patient monitoring system.

FIG. 2 shows a patient monitoring system that incorporates the patient monitoring device 12 along with a higher-level control (HLC) computer 20. The patient monitoring device 12 includes a processor 22, a gyroscope (GYRO) 24, a battery 26, and wireless communications circuitry (COMM) 28. In operation, the battery 26 supplies operating power to the other components as required. The gyroscope 24 senses three-axis motion and generates respective output signals that are provided to the processor 22. The communications circuitry 28 carries out wireless communications with the HLC computer 20, using so-called "Wi-Fi" for example. The processor 22 executes computer program instructions to receive and analyze the signals from the gyroscope 24 in order to detect patient movements, as described more below, and uses the communications circuitry 28 to communicate the detection of patient movements to the HLC computer 20.

The processor 22 may implement a data collection loop that polls the gyroscope 24 at a particular desired rate, e.g., 100 Hz, and may average or otherwise filter the samples. In one example, the raw samples are averaged over an interval of 50 samples, leaving a data representation of 2 Hz. The gyroscope 24 returns the rate of rotation for the three axes simultaneously, and the microprocessor-based program computes an integral of the angular velocity with reference to an initial known position over a period of 10 seconds for each stream to give the angular body positions in the three axes: pitch, yaw, and roll. At the end of a sampling period, a sample average may be written to a serial line before resetting to zero. The software may also correct for zero-error using a zero-threshold.

Figure 3:
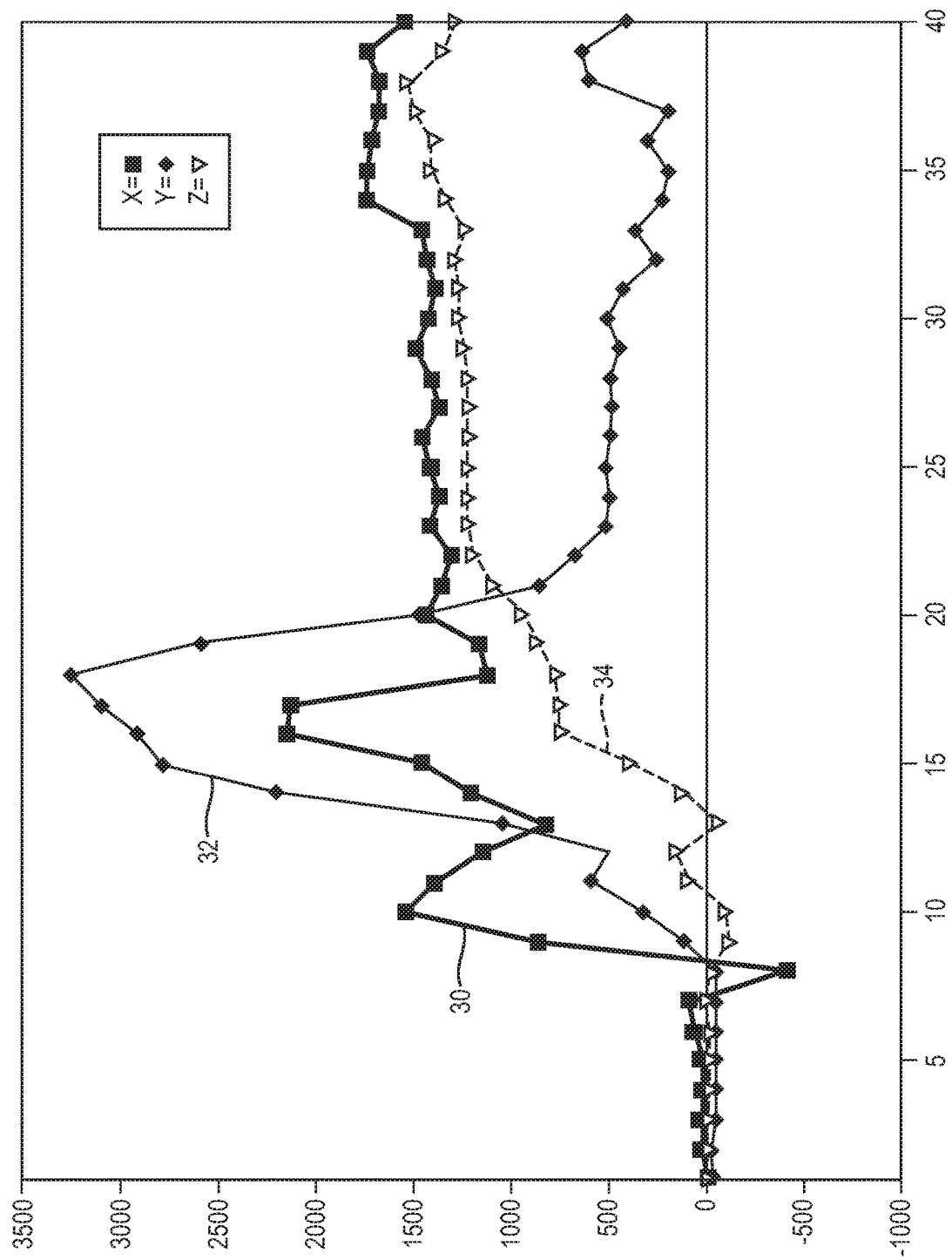
FIG. 3 is a plot of respective sensor output signals for a get-out-of-bed (GOB) movement.

FIG. 3 shows an example of sets of samples of the gyroscope output signals over a suitable period, such as 20 seconds. Sample values are in a range shown as [−1000, 3500](arbitrary units). In this example the data points represents samples taken at 2 Hz, and the data points may be averaged or filtered to reduce noise. Pitch, roll and yaw values are plotted at 30, 32 and 34 respectively. In the description below these dimensions may also be referred to as x, y and z respectively.

Figure 4:
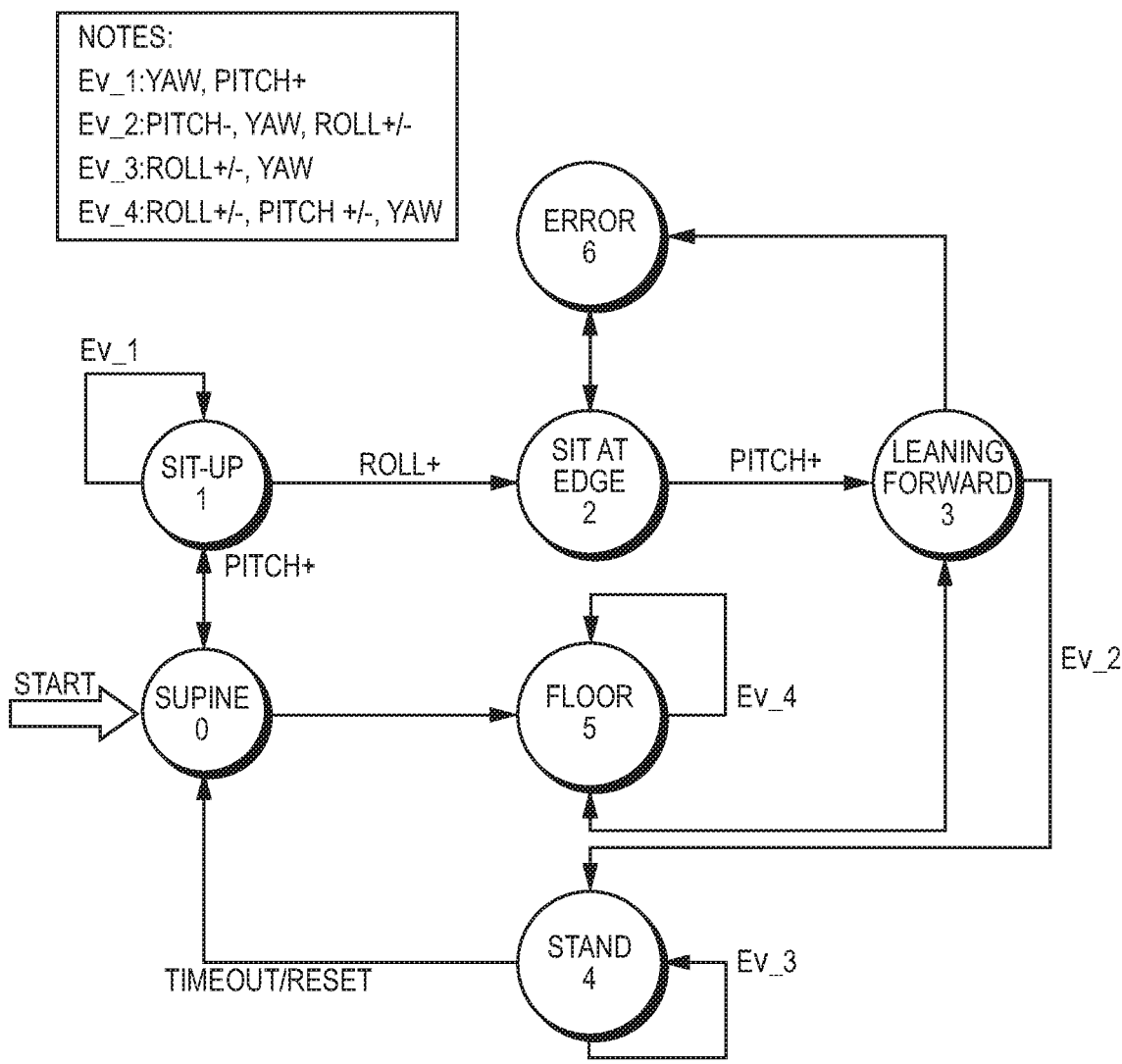
FIG. 4 is a finite state machine (FSM) representation of a GOB movement.

FIG. 4 shows an FSM model for a GOB detection template. States are represented by circles, and transition events are represented by arrows. Operation based on this template is described more below.

Protocols and Data Acquisition

Epoch Detection

The disclosed technique employs time periods referred to as "epochs" during which there is sensed activity that may be declared as a detected movement (e.g., GOB movement). Epochs may be established by obtaining and analyzing sensor data in a training phase in which one or more subjects perform the movement to be detected. In one example an epoch-detection method sweeps a pitch threshold ranging from 0 to 4000 in steps of 500. The pitch and roll values from the sensor crosses the threshold from lower to higher for greater than two seconds to detect the activity/movement (e.g., GOB movement).

Template-Based Detection

As indicated, a training data set may be used to train the sensor system to detect a certain movement. The training set protocol may include a sequence of defined movements that a subject is made to perform, and the sequence may be repeated to capture normal variations. Training the system helps to prevent false negatives, i.e., instances in which the system fails to detect a true event. Training data may be collected by having the subject wear the monitoring device 12 and perform consecutive movements, such as GOB movements each beginning in a supine position.

Data Processing and Template Matching Algorithm

Referring again briefly to FIG. 3, the pitch 30, roll 32, and yaw 34 traces on the graph correspond to the pitch 30, roll 32, and yaw 34 of the monitoring device 12. Sensor data collected for the "Getting Out of Bed" scenario shows that the x-coordinate increases first, followed by the y-coordinate and then a slight increase in the z-value. The initial increase of x corresponds to the individual sitting up in bed; the following increase of y corresponds to the individual turning to the side; and the final increase of z represents yaw from the individual's walking strides. These separate signals can thus be mapped to a certain movement pattern.

Each state in the activity detection process defines a specific epoch, or body configuration. The system analyzes the transitions between epochs in order to determine the activity being performed. Since the gyroscope 24 only measures angular rate of change, the signals are integrated over a running window to smooth the data. Each epoch corresponds to a scenario such as GOB that can be viewed as a sequence of movements. Hence, the system uses an FSM to identify the movement sequence. Referring to the example of FIG. 4, the FSM works like a flowchart that starts at State 0 and moves through the states via transitions that correspond to movements such as pitch, roll, and yaw. The transitions are triggered based on the values of certain parameters, as explained more below.

FIG. 4 shows, for the specific example of a GOB movement, an FSM having states 0 through 6 and associated transitions. The parameters that control transitions include gob_st_th (min threshold for pitch), rel_xy_th (max ratio of the roll to the pitch) and sway_parameter (min yaw). For example, when the subject pitches forward from an initial supine position, gob_st_th is crossed, and the state moves from State 0 to State 1 (transition shown as "Pitch+"). For the entire GOB movement performed normally, the FSM moves through states 0, 1, 2, 3 and 4, which correspond to Supine, Sit-up, Sit at edge, Leaning forward, and Stand respectively. If the subject were to get of bed abnormally, such as falling before getting up, the FSM might move to State 5 (Floor) before coming to the final state. Thus, the FSM model allows for multiple sets of state transitions before the event is classified as a GOB event.

For the real-time FSM, the transitions correspond to the phases of the sensor data graph versus time. The states of the FSM capture different key points in the graphs of the multiple sensors. For example, the states in FIG. 4 correspond to events such as: 1: "y has increased"; 2: "x has increased"; 3: "x has peaked but not y"; 4: "x and y have both peaked"; etc.

A template-matching method attempts to match data from a sensor to a pattern, or template, which is representative of an activity. Epoch-detection is a form of template-matching where an activity is modeled as a sequence of epochs that are then detected to identify the activity. One way of identifying the epochs is through curve-fitting, and another way is using threshold crossings, which is computationally more efficient than a curve fitting method. A method for epoch detection that is based on a Finite State Machine (FSM) identifies states in the shape of a curve that reflects the evolution of an activity.

Threshold-Based Epoch Detection

In one epoch detection method, two criteria are used: threshold and timeframe. The results of an epoch-based detection study may be assessed using a Receiver Operating Characteristic (ROC) curve. The epoch detection mechanism may first determine whether the pitch and the roll motions of the GOB event both cross a certain threshold. An example threshold is 2000, which may be broadly applicable to many different patients/subjects. The second criterion is timeframe: in order for the event to be classified as a GOB event, the motions in the GOB event have to take a certain minimum time (e.g., at least two seconds) to complete. The timeframe criterion is implemented in order to validate that the event taking place is a complete GOB event, and not just some sudden, non-GOB movement.

FSM-Based Epoch Detection

Another approach to epoch detection is a Finite State Machine (FSM)-based template-matching algorithm, an example of which is given above. The FSM detects an activity using a combination of state memory together with event triggers based on threshold crossings in identifying the movement. An advantage is that an FSM can distinguish multiple sequences of events that comprise the activity, improving the sensitivity of detection. Hence, it is more effective at detecting the GOB events than a pure threshold-based epoch detection and is computationally less intensive than a graph-matching epoch detection.

In one example, an FSM-based template matching algorithm can be assessed by calculating sensitivity and specificity of the system. The sensitivity may be defined as TP/(TP+FN), and the specificity is defined as TN/(TN+FP), where a TP (True Positive) means both the sensor and an expert outputted T; TN (True Negative) means both outputted F; FP (False Positive) means the sensor detected T while it was actually F; and FN (False Negative) means the sensor detected F while it was actually T.

An FSM-based template-matching algorithm can be effective in the detection of a motor activity. A sensing algorithm as described herein may be more accurate in detecting events that are related to the normal GOB event. The system can be trained using a data particular to the GOB activity, and may be tested against other (non-GOB) activities to evaluate its rate of false positives. In one example, sensitivity may be determined to be $5/(5+4)=0.56$, and specificity $21/(21+5)=0.81$, where sensitivity is the proportion of actual GOB events that are detected and specificity is the proportion of non-GOB events that are correctly identified as non-GOB. This may be evaluated by having a subject perform non-GOB activity such as household chores for a certain period (e.g., one hour).

Figure 5:
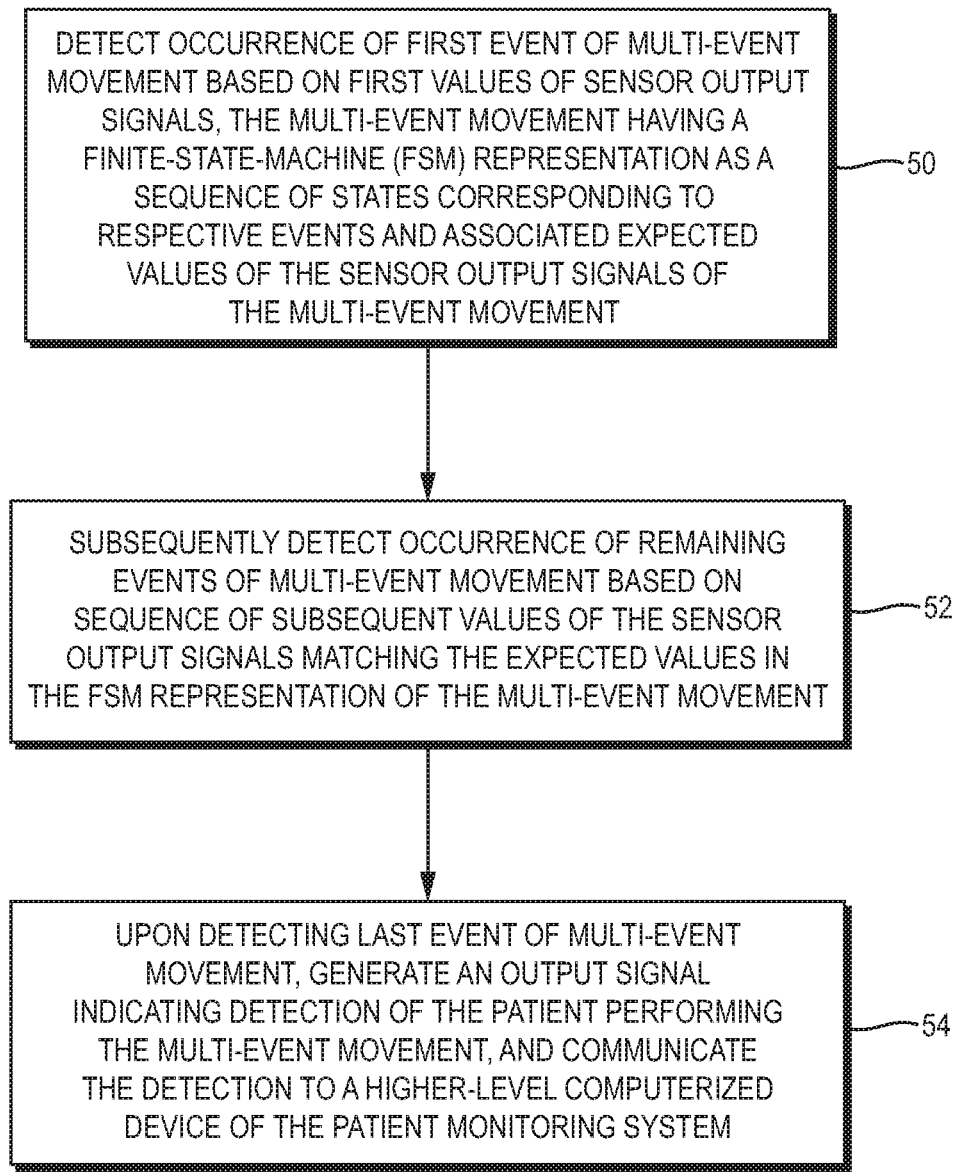
FIG. 5 is a flow diagram of high-level operation.

FIG. 5 is a high-level flow diagram of operation of the patient monitoring device 12, specifically of the template-matching monitoring process implemented by the processor 22 with involvement of other components.

At 50, the occurrence of a first event of a multi-event movement is detected based on first values of the sensor output signals, where the multi-event movement has a finite-state-machine (FSM) representation as a sequence of states corresponding to respective events and associated expected values of the sensor output signals of the multi-event movement. In one example the multi-event movement is a GOB movement such as described above, with the first event being a first transition of body configuration (e.g., pitching forward to the Sit-up position of State 1).

At 52, there is subsequently detection of the occurrence of remaining events of the multi-event movement based on a sequence of subsequent values of the sensor output signals matching the expected values of the sensor output signals in the FSM representation of the multi-event movement. In the above GOB example, these correspond to the transitions to states 2, 3 and 4 for example.

At 54, upon detecting a last event of the multi-event movement, an output signal is generated indicating detection of the patient performing the multi-event movement, and the detection of the multi-event movement is communicated to a higher-level computerized device (e.g., HLC computer 20) of the patient monitoring system.

Applications

The wearable sensor system can have a beneficial impact on patient care in a hospital setting. Specifically, this system can be implemented for fall prevention of the elderly in a nursing home as well as convalescent patients in post-operation recovery. The elderly may be susceptible towards falls because they may lack the ambulatory skills and may be disoriented, while convalescent patients may have impaired awareness or balance due to the influence of drugs. Due to the large number of patients that doctors and nurses deal with on a day-to-day basis, they may encounter multiple issues with the current system, including alarm fatigue and forgetting to turn the bed pressure sensor back on after it has gone off. A continuous monitoring system with smart, algorithmic detection is preferred in these situations.

A template-matching approach can be a way to improve the sensitivity of GOB detection. The epoch-detection method requires having an a priori specific knowledge of a reference pattern—that is difficult to know because of the variation from one GOB event to another within the same individual and across individuals. Using a single threshold (such as 2000, as mentioned above) causes a lower sensitivity; therefore, a template-matching technique was explored for improving sensitivity. The technique uses an FSM, which tracks the states and transitions within the movement that corresponds to a particular motion template. This algorithm uses noticeable patterns in sensory data to determine transitions between different body configurations.

Study has demonstrated the efficacy of the FSM-based template matching detection as an improvement over epoch-based detection, which may have a lower sensitivity because it is difficult to determine one threshold that accurately detects all the different GOB events. Also, the epoch-detection method based on graph matching is difficult to implement in real-time due to the high amount of processing required to scale the graphs and match the patterns. In contrast, the FSM-based method has only minimal amount of state to be maintained, and yet can offer quick and accurate detection of the GOB scenario.

FSM-based detection can be effectively applied in detecting other types of movements as well. This is because the FSM allows a complex movement to be broken down into sub-movements that are more easily detectable. One such activity that might benefit from such a detection method is the quick recovery using monitored rehabilitation treatment. For even more complex activities, an additional sensor such as an accelerometer may help in providing other event-specifying information.

The FSM-based detection method is able to detect events in real-time using a modified FSM, where the transitions are defined based on the phases of the sensor data rather than any specific sub-movement. Using this approach, alerts can be relayed in real-time to an application on an attendant's cell phone or a monitoring station, which may be desirable for fall prevention.

The description herein contains several specifics for compliance with disclosure requirements. The invention is not necessarily limited to any particular implementation of its different aspects. The following are two specific areas of more general applicability of the invention:
  1. The ability to detect motions other than getting out of bed by employing the Finite State Machine (FSM) method for detection
     an action can be viewed as a sequence of movements
     the method can be used to detect complex movements in sports, such as a jump shot in basketball, blocking or tackling in football, or a soccer kick
     the method can also be used in patient rehabilitation, to keep track of a patient's range of motion—for example, it can provide feedback to a patient in post-ACL reconstruction surgery rehab so the user can gradually increase his/her range of motion through feedback from the app for a faster rehabilitation
  2. Other alternatives
     using a different type of microprocessor other than Arduino
     using other sensors such as an accelerometer
     using multiple sensors combined to assist the FSM
     continuously monitoring and analyzing in real time to determine trends in the progress of treatment While various embodiments of the invention have been particularly shown and described, it will be understood by those skilled in the art that various changes in form and details may be made therein without departing from the spirit of the invention as defined by the appended claims.

What is claimed is:

1. A wearable patient monitoring device for use in a patient monitoring system, comprising:
one or more motion sensors generating respective sensor output signals in response to sensed motion of a patient wearing the patient monitoring device, the motion sensors including a gyroscope for sensing rotation of the patient's body about a pitch axis, a roll axis, and a yaw axis, and for generating the sensor output signals to include respective rates of rotation of the patient's body about the respective axes; and
a processor coupled to the gyroscope to receive and process the sensor output signals according to a template-matching monitoring process, the template matching process including:
detecting occurrence of a first event of a multi-event movement based on first values of the sensor output signals, the multi-event movement being a get-out-of-bed movement having a finite-state-machine (FSM) representation as a sequence of states corresponding to respective events and associated expected values of the sensor output signals of the multi-event movement, the first event being a sit-up event identified by the sensor output signals indicating positive rotation about the pitch axis by an amount above a predetermined initial pitch threshold;
subsequently detecting occurrence of remaining events of the multi-event movement based on a sequence of subsequent values of the sensor output signals matching the expected values of the sensor output signals in the FSM representation of the multi-event movement, the remaining events including a leaning-forward event followed by a stand event, identified by the sensor output signals first indicating positive rotation about the pitch axis followed by the sensor output signals indicating negative rotation about the pitch axis; and
upon detecting a last event of the multi-event movement, generating an output signal indicating detection of the patient performing the multi-event movement; and
communications circuitry configured and operative in response to the output signal to communicate the detection of the patient performing the multi-event movement to another computerized device of the patient monitoring system.

2. The wearable patient monitoring device of claim 1, employing a modified FSM to detect events in real time, with transitions between states being defined based on phases of the sensor signals.

3. The wearable patient monitoring device of claim 2, wherein the communications circuitry is further configured and operative to relay alerts in real-time to an application on an attendant's device or a monitoring station.

4. The wearable patient monitoring device of claim 1, wherein the sequence of states includes a sequence Supine, Sit-Up, Sit at Edge, Leaning Forward, and Stand, and wherein (i) a transition from Sit-Up to Sit at Edge is based on the sensor output signals indicating positive rotation about the roll axis and (ii) a transition from Sit at Edge to Leaning Forward results from the leaning-forward event.

5. The wearable patient monitoring device of claim 4, wherein the sequence of states includes a Floor state reached from the Leaning Forward state in response to the patient falling to the floor before standing.

6. The wearable patient monitoring device of claim 4, wherein a transition from Stand to Supine occurs in response to a timeout or reset.

* * * * *